United States Patent [19]

Kieturakis

[11] Patent Number: 5,630,813

[45] Date of Patent: May 20, 1997

[54] ELECTRO-CAUTERIZING DISSECTOR AND METHOD FOR FACILITATING BREAST IMPLANT PROCEDURE

[76] Inventor: Maciej J. Kieturakis, 372 Beverly Dr., San Carlos, Calif. 94070

[21] Appl. No.: 352,335

[22] Filed: Dec. 8, 1994

[51] Int. Cl.⁶ .................................................. A61B 17/36
[52] U.S. Cl. ............................ 606/46; 606/29; 606/41; 606/191; 607/101
[58] Field of Search ........................ 606/27–34, 37–42, 606/45–50, 190–192; 607/100–102, 104, 122; 128/642, 898; 604/113, 114; 600/114–116

[56] References Cited

U.S. PATENT DOCUMENTS

| | | |
|---|---|---|
| 936,379 | 10/1909 | Stevens . |
| 3,096,962 | 7/1963 | Meijs . |
| 4,191,191 | 3/1980 | Auburn . |
| 4,535,773 | 8/1985 | Yoon ............................. 604/51 |
| 4,601,710 | 7/1986 | Moll ............................. 604/165 |
| 4,654,030 | 3/1987 | Moll et al. .................... 604/165 |
| 4,784,133 | 11/1988 | Mackin ......................... 600/116 |
| 4,836,205 | 6/1989 | Barrett . |
| 4,867,404 | 9/1989 | Harrington et al. . |
| 4,881,537 | 11/1989 | Henning ........................ 604/84 |
| 4,913,142 | 4/1990 | Kittrell et al. .................. 606/7 |
| 4,998,933 | 3/1991 | Eggers et al. .................. 606/31 |
| 5,019,075 | 5/1991 | Spears et al. .................. 606/28 |
| 5,116,353 | 5/1992 | Green ........................... 606/184 |
| 5,147,316 | 9/1992 | Castillenti .................... 604/164 |
| 5,147,376 | 9/1992 | Pianetti ......................... 606/170 |
| 5,156,151 | 10/1992 | Imran ............................ 128/642 |
| 5,201,325 | 4/1993 | McEwen et al. . |
| 5,203,773 | 4/1993 | Green ........................... 606/104 |
| 5,209,736 | 5/1993 | Stephens et al. .............. 604/164 |
| 5,224,952 | 7/1993 | Deniega et al. ............... 606/184 |
| 5,226,890 | 7/1993 | Ianniruberto et al. ......... 604/164 |
| 5,232,451 | 8/1993 | Freitas et al. ................. 606/174 |
| 5,255,678 | 10/1993 | Deslauriers et al. .......... 607/122 |
| 5,258,003 | 11/1993 | Ciaglia et al. ................. 606/185 |
| 5,271,380 | 12/1993 | Riek et al. . |
| 5,279,567 | 1/1994 | Ciaglia et al. ................. 604/117 |
| 5,284,130 | 2/1994 | Ratliff . |
| 5,311,866 | 5/1994 | Kagan et al. .................. 607/122 |
| 5,312,357 | 5/1994 | Buijs et al. .................... 604/164 |
| 5,334,185 | 8/1994 | Giesy et al. ................... 604/164 |
| 5,336,237 | 8/1994 | Chin et al. ..................... 606/167 |
| 5,346,504 | 9/1994 | Ortiz et al. ..................... 606/192 |
| 5,348,541 | 9/1994 | Lyell ............................. 604/164 |
| 5,368,598 | 11/1994 | Hasson . |
| 5,370,109 | 12/1994 | Cuny . |
| 5,445,142 | 8/1995 | Hassler, Jr. .................... 600/114 |

*Primary Examiner*—Angela D. Sykes
*Assistant Examiner*—Michael Peffley
*Attorney, Agent, or Firm*—Skjerven, Morrill, MacPherson, Franklin & Friel; Norman R. Klivans

[57] ABSTRACT

An inflatable dissector and method for bluntly dissecting and electro-cauterizing a plane between the anterior chest wall and the overlying pectoralis major muscle to facilitate a breast implant procedure. The instrument includes an elongate blunt-tipped probe member and carries a distal expandable sleeve with an electrode grid on its surface. The blunt tip of the guide is advanced distally along a plane in the interior of the body thereby creating a small diameter dissected track. The distal inflatable sleeve is expanded to dissect the plane and an electrical current is introduced into the electrode grid to cauterize around the surface of the dissected space. A dual-port cannula assembly and an electro-cauterizing "inside-out" trocar are provided to safely make an additional incision under endoscopic vision from the inside of the dissected plane to the outside of the body from a single skin incision.

16 Claims, 10 Drawing Sheets

ELECTRO-CAUTERIZING DISSECTOR AND METHOD FOR FACILITATING BREAST IMPLANT PROCEDURE

CROSS-REFERENCE TO RELATED APPLICATIONS

This application is related to and commonly invented U.S. patent application Ser. No. 08/334,656 filed Nov. 3, 1994 (now abandoned) which is incorporated herein by reference. This application also is related to and commonly invented U.S. patent application Ser. No. 08/255,273, filed Jun. 1, 1994, now U.S. Pat. No. 5,569,183, which is incorporated herein by reference.

BACKGROUND OF THE INVENTION

1. Field of the Invention

This invention relates to surgical instrumentation and more particularly to an instrument and method for dissecting and contemporaneously cauterizing a plane in the interior of the body to create a relatively blood-free dissection.

2. Description of Prior Art

In breast reconstruction or breast augmentation procedures, at times an implantable prosthesis is placed against the anterior chest wall underlying the pectoralis major muscle. In current practice, the pectoralis major muscle is dissected away from the chest wall though an open surgery which may be time-consuming.

SUMMARY OF THE INVENTION

The instrument in accordance with the present invention is adapted for dissecting connective tissues in planes around a muscle and electro-cauterizing the dissected plane and is described with reference to the exemplary method of dissecting and cauterizing a plane between the pectoralis major muscle and the chest wall. The instrument includes an elongate 10 mm. diameter blunt-tipped probe member that is used to bluntly dissect a pathway along a plane underlying the pectoralis major muscle. The instrument includes an optic lumen affording the surgeon contemporaneous endoscopic vision through the transparent distal tip of the probe as it is pushed along the plane. Optic fibers transmit light through the distal tip of the probe to illuminate the plane being dissected. An insufflation channel is provided to insufflate the dissected plane in front of the instrument's tip to enhance endoscopic vision during insertion of the probe. The distal portion of the dissector carries an inflatable elastomeric sleeve that incorporates around its surface a grid of bi-polar electrodes to cauterize dissected blood vessels. The instrument is made of plastic, including inexpensive plastic optics, and may be disposable.

In performing a method in accordance with the present invention in an exemplary procedure, the surgeon makes a small incision lateral to the breast. The surgeon then identifies the plane underlying the pectoralis major muscle and overlying the chest wall and advances the tip of the probe inward along the plane thus bluntly dissecting a small-diameter track while contemporaneously viewing (on a video monitor) the plane being dissected in front of the probe tip. The surgeon stops advancing the tip and then introduces an inflation medium into the inflatable sleeve to further dissect the plane. The dissected plane under the pectoralis major muscle is profuse with veins and capillaries which may be severed by the dissection. With the inflatable sleeve in an expanded state, the outward pressure of the sleeve causes hemostasis within the dissected plane. However, if the sleeve were collapsed, the plane could be contaminated with blood. To maintain a relatively blood-free dissection, the surgeon introduces an electrical current through a bi-polar electrode grid fixed around the sleeve's surface to cauterize dissected blood vessels. The current is introduced sequentially around the sleeve to control the heating of tissue. The surgeon then deflates the inflatable sleeve and again advances the probe thus bluntly dissecting a further small-diameter track. Thereafter, the sleeve again is inflated and the dissected region again is cauterized. By repeating the procedure several times, the surgeon is able to dissect and cauterize the entire plane underlying the pectoralis major muscle through a single minimally invasive incision.

The surgeon may introduce an accessory instrument into the dissected plane with a dual-port cannula assembly in accordance with the present invention. The dual-port cannula assembly is adapted for use in a single incision of any size ranging from 1 to 3 cm. in length and includes a 10–12 mm. port flexibly connected to a 5 mm. port. Thus, an endoscope and another instrument may be introduced into the dissected plane through a single incision.

If yet another instrument is required, along with an endoscope, the surgeon may insufflate the dissected plane and safely make an additional incision for another cannula assembly by utilizing the electro-cauterizing (EC) "inside-out" trocar in accordance with the present invention. The EC "inside-out" trocar allow incisions to be made safely from within a confined insufflated space outwardly through the skin under direct endoscopic vision, rather than plunging a conventional trocar from outside the body into the confined space. An "inside-out" trocar first was disclosed in application Ser. No. 08/255,273, referenced above. The improvement disclosed herein relates to the incorporation of a mono-polar electrode into the trocar tip that allows the additional incision to be made with little outward pressure while at the same time cauterizing the incision. After the tip of the EC trocar is disposed outside the skin, a second cannula assembly may be pushed into the additional incision using the trocar shaft as a guide.

The presently disclosed inflatable electro-cauterizing sleeve is to be contrasted with the disclosure of Ser. No. 08/334,656, referenced above. Ser. No. 08/334,656, discloses a "retrograde" dissector in which an elongate probe is utilized to bluntly dissect a small-diameter "track" along a plane between muscle layers and thereafter the "retrograde" (reverse) movement of an expanded inflatable structure within the dissected "track" further dissects a plane in the interior of the body along lines of least resistance.

The presently disclosed inflatable electro-cauterizing sleeve is also to be contrasted with the disclosure of Ser. No. 08/255,273, referenced above. Ser. No. 08/255,273 discloses an elongate probe with a transparent inflatable envelope that is expanded in a fixed location to bluntly dissect a viewing space in the interior of a body. Ser. No. 08/255,273 discloses a method for endoscopically viewing a surgical procedure performed around the surface of the transparent expanded envelope and is described with reference to a spinal nerve division.

The presently disclosed inflatable electro-cauterizing sleeve also is to be contrasted with co-pending Ser. No. 07/893,988 of Kieturakis and Mollenaur which disclosed a large volume low-pressure non-elastomeric balloon that is carried into the interior of the body and inflated in a fixed position. The large balloon of Ser. No. 07/893,988 is suitable for dissecting the peritoneum (a thin membrane) away from the abdominal wall to create a space to be insufflated. Ser. No. 07/893,988 disclosed a method of performing a surgical procedure (i.e., a hernia repair) in the insufflated preperitoneal space.

In general, in accordance with the present invention, an elongate probe member is used in method for bluntly dissecting connective tissues along a plane of least resistance in the interior of the body between a first location and a second remote location and for expanding an inflatable electro-cauterizing sleeve in the remote location to further bluntly dissect and cauterize the dissected plane to provide a relatively bloodless dissection. A bipolar electro-cauterizing grid is provided on the surface of the inflatable sleeve to moderate the heating of tissue. An electrical source introduces current sequentially to electrodes around the circumference of the sleeve thereby causing an electro-cauterizing effect that "floats" around the inflated sleeve to further moderate heating of tissues.

Advantageously, the present instrument and method allow contemporaneous vision through the probe member as it traverses a plane from the first location to the second remote location. The present instrument and method allow contemporaneous insufflation of the dissected plane as the probe traverses a plane from the first location to the second remote location.

The present dual-port cannula assembly and method advantageously allow an endoscope and an accessory instrument to be introduced into an endoscopic workspace through a single small incision. Also provided is a resilient coupling between first and second ports thus allowing a degree of freedom of movement between an endoscope and an accessory instrument. Also provided is an improved skin seal for making a fluid-tight seal within a skin incision ranging in length from 1 cm. to 3 cm. Also provided is an improved skin seal that allows a tubular port to be adjusted for depth within the skin seal by sealably sliding the port within a passageway in the distensible skin seal member. Also provided is a simplified instrument seal for a cannula bore seal made of a plurality of elastomeric planar elements.

Also provided is an electro-cauterizing "inside-out" trocar that allows incisions to be made safely from the inside of an insufflated space outwardly through the skin under direct endoscopic vision.

Also provided is an instrument that is inexpensive and may be disposable. Additional advantages and features of the present invention will appear in the following description.

DESCRIPTION OF THE DRAWINGS

FIGS. 17A–17C are sectional views of a patient's chest showing the manner in which the cannula assembly of FIG. 9 is utilized to perform an exemplary method of the present invention.

DETAILED DESCRIPTION OF THE INVENTION

1. Electro-Cauterizing Inflatable Dissector

By way of example, FIGS. 1–4 illustrate electro-cauterizing (EC) dissector 5 adapted for a breast implant procedure. EC dissector 5 has elongate plastic probe sleeve 10 with proximal and distal ends, 11 and 12. Probe sleeve 10 with central bore 14 preferably is made of transparent medical grade plastic. The overall length of probe sleeve 10 along axis 15 for a breast implant procedure is approximately 250 mm. (not limiting). The diameter of probe sleeve 10 is approximately 10 mm. (not limiting). Distal end 12 of sleeve 10 has a rounded or blunt transparent tip 17 enclosing bore 14. The distal portion 18 of sleeve 10 has a reduced diameter to accommodate the thickness of wall 19 of inflatable elastomeric sleeve 20 described further below. Inflatable sleeve 20 in a "sleeve-contracted" state contracts to the outer diameter of probe sleeve 10 (see FIG. 1).

Figure 1:
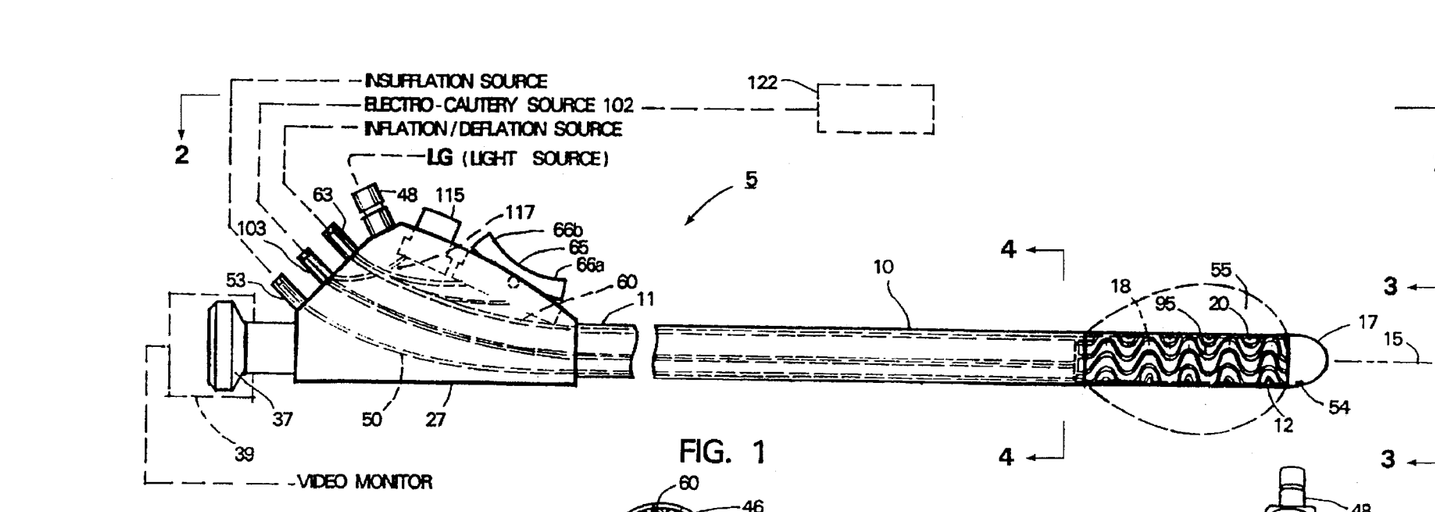
FIG. 1 is a side elevational view of the dissector of the present invention.
Figures 2, 3, 4:
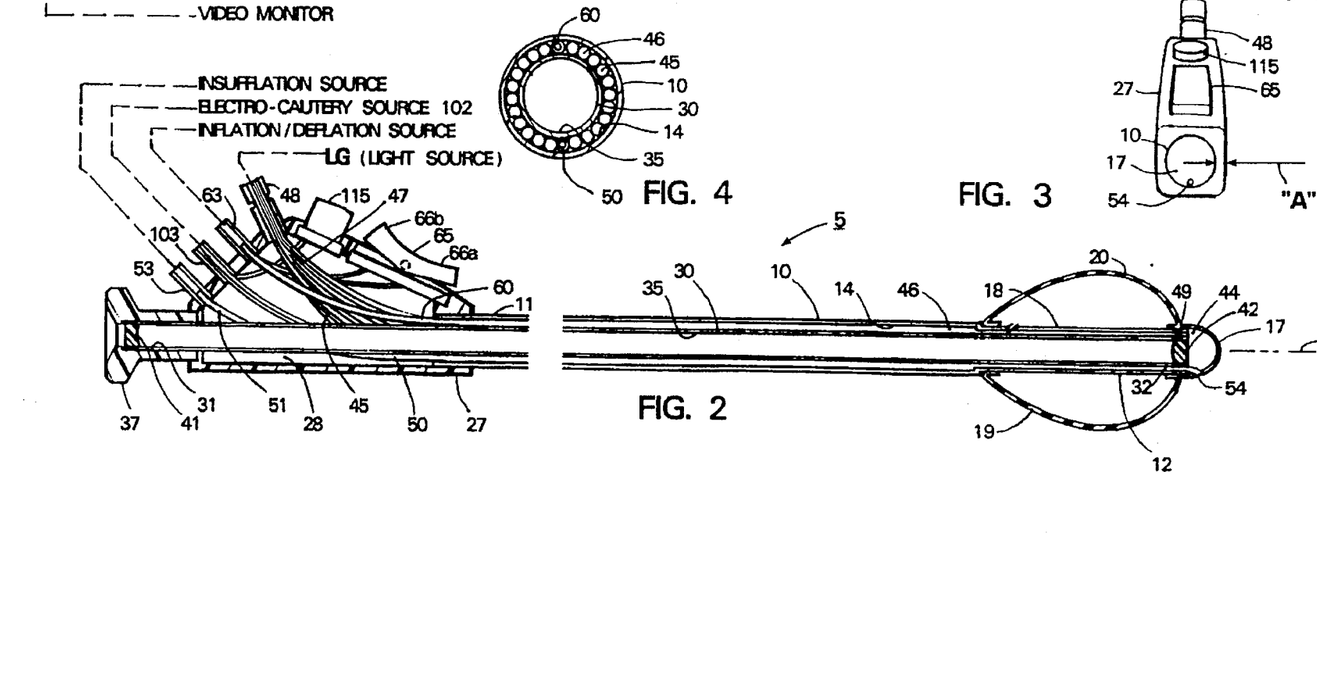
FIG. 2 is a longitudinal partial sectional view of the instrument of FIG. 1 taken along line 2—2 of FIG. 1 rotated 90°.
FIG. 3 is end elevational view of the instrument of FIG. 1 taken along line 3—3 of FIG. 1.
FIG. 4 is a transverse sectional view of the instrument of FIG. 1 taken along line 4—4 of FIG. 1.

FIGS. 1–2 show handle 27 made of plastic mating halves that are joined by any suitable means such as adhesives and form hollow handle interior 28. Proximal end 11 of probe sleeve 10 is fixed in the distal portion of handle 27. FIG. 3 is an end elevational view of handle 27 illustrating its three flat sides that extend radially outward a minimal dimension "A" beyond the diameter of probe sleeve 10 for reasons explained below. The maximum dimension "A" preferably is 2 to 3 mm. or less.

Referring to FIGS. 2 and 4, optic sleeve 30 with proximal and distal ends, 31 and 32, is made of thin-wall metal or plastic and extends through instrument 5. Sleeve 30 has central bore 35. Proximal end 31 of optic sleeve 30 is fixed in plastic molded eyepiece 37 in the proximal portion of handle 27. Eyepiece 37 is dimensioned to fit to a standard endoscopic video camera 39 shown in phantom view in FIG. 1 to allow the surgeon to operate EC dissector 5 while viewing a video monitor. Proximal and distal lens elements, 41 and 42, are disposed in the respective proximal and distal ends of bore 35 to provide a suitable field of vision through the bore. Other lens elements (not shown) may be required to provide a suitable field of vision and depth of field. Space 44 is provided between distal lens element 42 and the interior of transparent blunt tip 17 of probe sleeve 10.

FIG. 4 illustrates a transverse sectional view of the EC dissector with approximately twenty-four (not limiting) optic fibers 45 serving as a light probe (LG). Optic fibers 45 ranging in diameter from 0.001" to 0.01" are dimensioned to fill the concentric interstitial space 46 around optic sleeve 30 and within bore 14 of probe sleeve 10. The proximal ends 47 (collectively) of optic fibers 45 are bundled and fixed in male fitting 48 in handle 27. A female push-connector (not shown) coupled to a conventional LG light source may be connected fitting 48. The distal ends 49 of optic fibers 47 are suitably finished for the transmission of light and are fixed in place with adhesives around distal end 32 of optic sleeve 30.

An insufflation mechanism delivers a gas or liquid through probe sleeve 10 and includes longitudinally-extending insufflation tube 50 that has a diameter similar to an optic fiber 45 (see FIG. 4). The proximal end 51 of tube 50 is fixed in Luer-type fitting 53 in handle 27. As can be seen in FIGS. 1-3, tube 50 has open distal termination 54.

Referring to FIGS. 1-2, inflatable sleeve 20 having inflation chamber 55 is disposed around reduced-diameter portion 18 of probe sleeve 10. Inflatable sleeve 20 is made of an elastomeric tubular material such as latex. The proximal end of sleeve 20 is sealably fixed to sleeve 10 by adhesives or other suitable means. The distal end of sleeve 20 is similarly sealably fixed to sleeve 10 providing a fluid-tight inflation chamber 55. As can be seen in FIGS. 1-2, blunt tip 17 of probe sleeve 10 is external to inflation chamber 55.

An inflation mechanism inflates sleeve 20 around probe sleeve 10 with an inflation medium, preferably $CO_2$ or other gas or saline solution. Referring to FIGS. 2 and 4, inflation tube 60 is disposed in interstitial space 46 between optic sleeve 30 and probe sleeve 10 and is similar in diameter to optic fibers 45. The open distal end of tube 60 communicates with inflation chamber 55 (see FIG. 2). The proximal end of tube 60 is fixed in Luer-type fitting 63 in handle 27. A conventional pressurized inflation/deflation source is provided to supply an inflation medium through fitting 63 to inflate or deflate chamber 55. Inflation trigger 65 is a rocker switch connected to electrical leads in which depression of trigger arm 66a causes pressurization and depression of trigger arm 66b causes de-pressurization (suction) of chamber 55.

Figure 5:
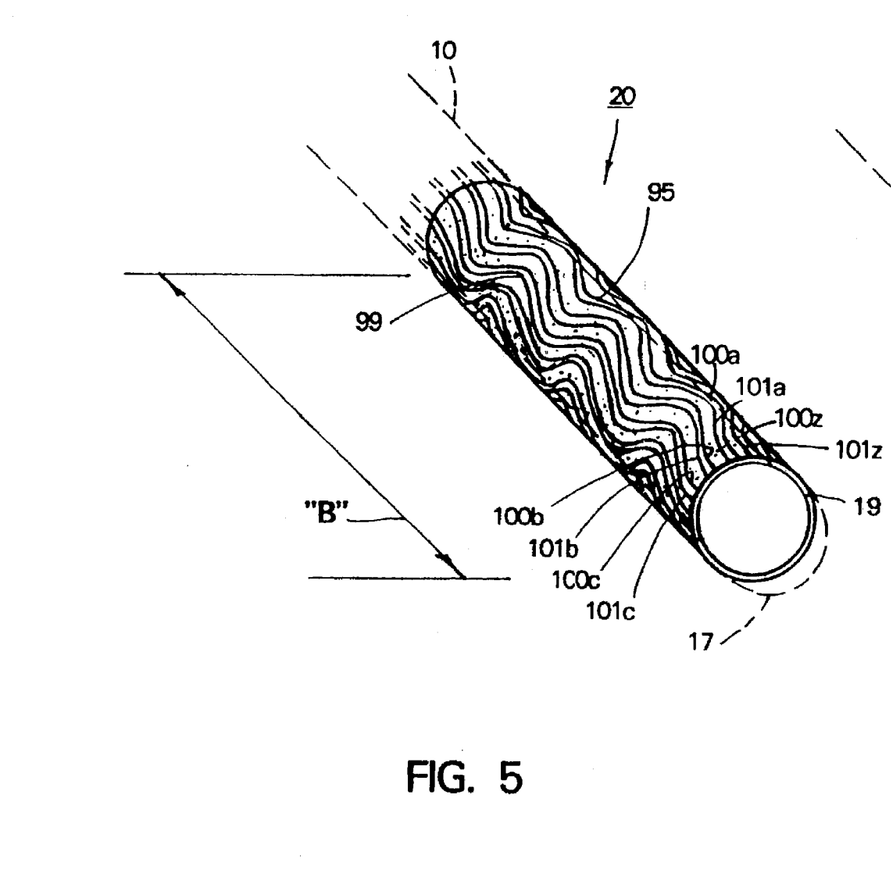
FIG. 5 is an axionometric view of the inflation sleeve of the instrument of FIG. 1 in a contracted state.
Figure 6:
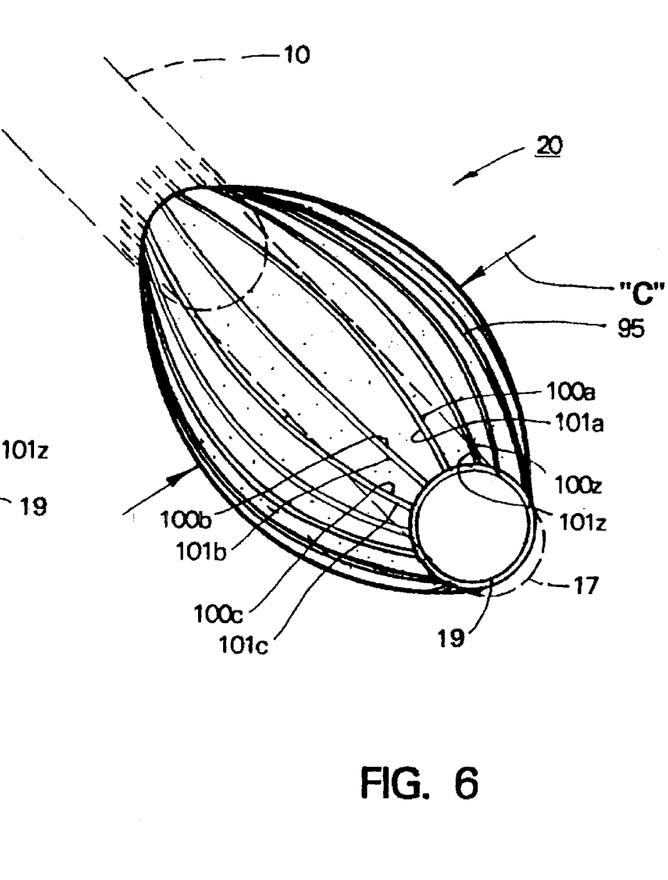
FIG. 6 is an axionometric view of the inflation sleeve of FIG. 5 in a fully expanded state.

Referring to FIGS. 5, inflatable sleeve 20 is shown in a "sleeve-contracted" state. FIG. 6 shows sleeve 20 in a "sleeve-expanded" state. In the axionometric view of FIG. 5, sleeve 20 can be seen to have a generally round or tubular sectional shape. However, a variable thickness latex wall 19 for sleeve 20 may be provided to induce the flattened sectional shape as disclosed in co-pending application Ser. No. 08/334,656 (abandoned) filed Nov. 3, 1994. Referring to FIG. 6, the preferred size of sleeve 20 for an electro-cauterizing dissection under a pectoralis major muscle has an axial dimension "B" ranging from 25 mm. to 75 mm. The preferred maximum radial dimension "C" in FIG. 6 in the sleeve's expanded position ranges from 25 mm. to 50 mm. (dimensions not limiting).

Referring to FIGS. 5-6, the outer surface of sleeve wall 19 has laminated thereon bi-polar electro-cautery grid 95 (collectively) made up of from 20 to 100 pairings of bi-polar EC electrodes 100a-100z and 101a-101z. (not limiting). By the term bi-polar, it is meant that each electrode 100a-100z is associated with an adjacent electrode 101a-101z to provide an electrical field that flows from one (positive) electrode to an adjacent (negative) electrode. Such bi-polar flow of an electrical current will tend to encase the surface of sleeve 20 with an electrical field that will cauterize dissected blood vessels around the sleeve's surface.

Bi-polar grid 95 of EC electrodes is preferred over a mono-polar grid (not shown) of EC electrodes because a bi-polar grid will generate less heat and insure that current has a directional flow, which will prevent perforation of wall 19 of inflatable sleeve 20. It should be appreciated that a mono-polar EC grid around the surface of sleeve 20 is within the scope of the present invention.

As depicted in FIG. 6, the electrodes generally are disposed in a longitudinal configuration when sleeve 20 is in the "sleeve-expanded" state. The EC electrodes are fixed to the exterior surface of sleeve 20 with adhesives. With sleeve 20 in a "sleeve-contracted" state as shown in FIG. 5, the electrode grid 95 deforms into a sinuous pattern 99 under the contracting force of the elastomeric material of sleeve wall 19. The EC electrodes may be made of a spring-like wire formed into a sinuous pattern and tensioned (straightened) over an expanded sleeve 20 disposed over a mandril and then laminated to the sleeve in manufacturing. The EC electrodes may have diameters ranging from 0.005" to 0.025" and be any suitable material for conducting an EC current.

Referring to FIG. 1, an EC electrical source 102 is provided and is coupled to fitting 103. EC wire bundle 110 in handle interior 28 has proximal and distal ends, 111 and 112, and is made up of bi-polar electrodes 100a-100z and 101a-101z. The distal end 112 of wire bundle 110 has the electrode pairings 100a-100z and 101a-101z, separated and thereafter disposed along with optic fibers 45 in interstitial space 46 and connected to EC grid 95 at the proximal end of sleeve 20 (see FIGS. 5-6). EC trigger 115 is adapted for actuation by finger pressure and is connected to EC source 102 by circuit wire 117. EC trigger 115 is urged to a closed position by a spring (not visible). It can be seen that upon depressing trigger 115, current will flow from EC source 102 through wire bundle 110 to the electrodes carried around sleeve 20.

The EC source 102 is coupled to an EC controller 122 that has electrical circuits to direct current sequentially to a single pair of electrodes at a time for a fraction of a second each. For example, an EC current is directed to EC electrode 100a for 1/100 second (not limiting), then to electrode 100b for 1/100 second, then to electrode 100c for 1/100 second and so on. By this sequencing, heat will build up slowly in the electrodes and the cauterization of dissected blood vessels will occur as current "floats" around the surface of an expanded sleeve 20.

2. Method of Use of Electro-Cauterizing Inflatable Dissector

Figure 7A:
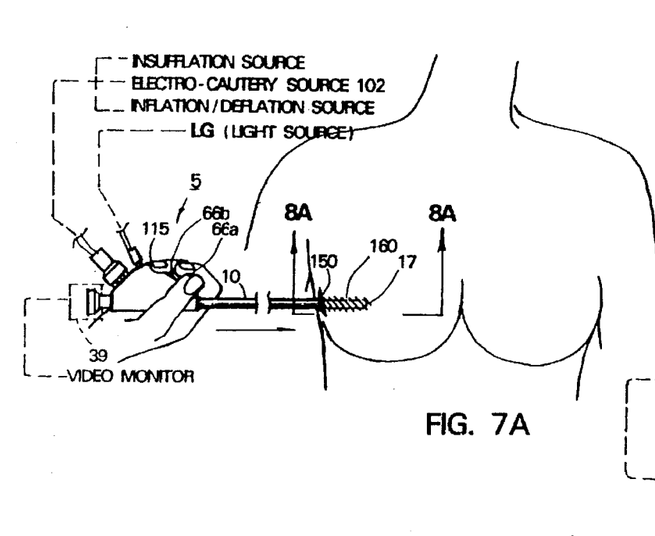
FIGS. 7A–7C are cartoons showing the manner in which the dissector of FIG. 1 is used to perform an exemplary method of the present invention.
Figure 7B:
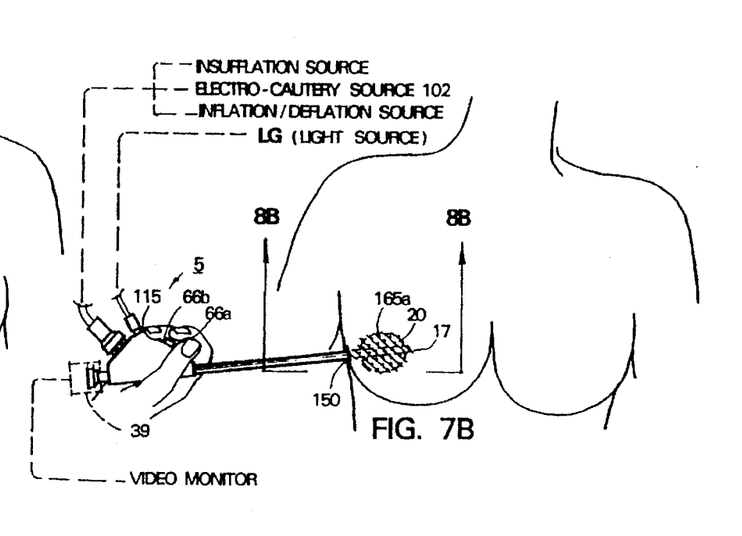
Figure 7C:
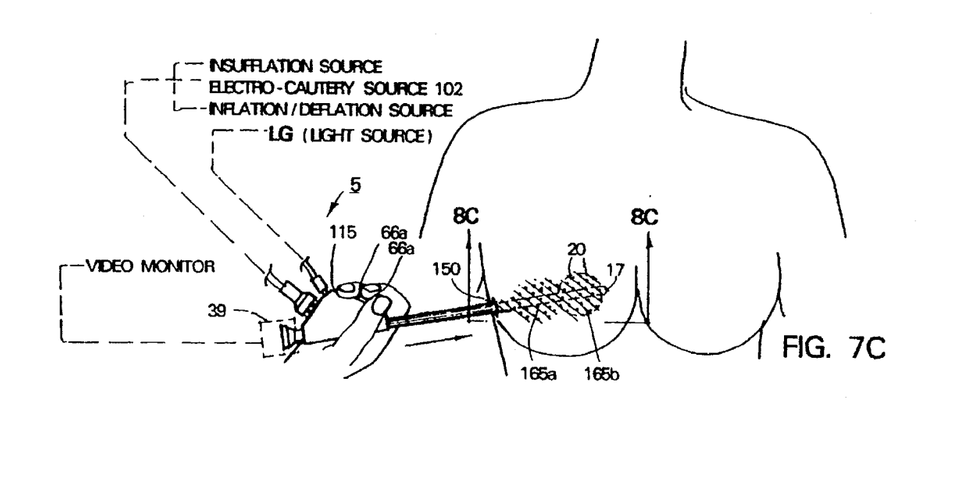
Figure 8A:
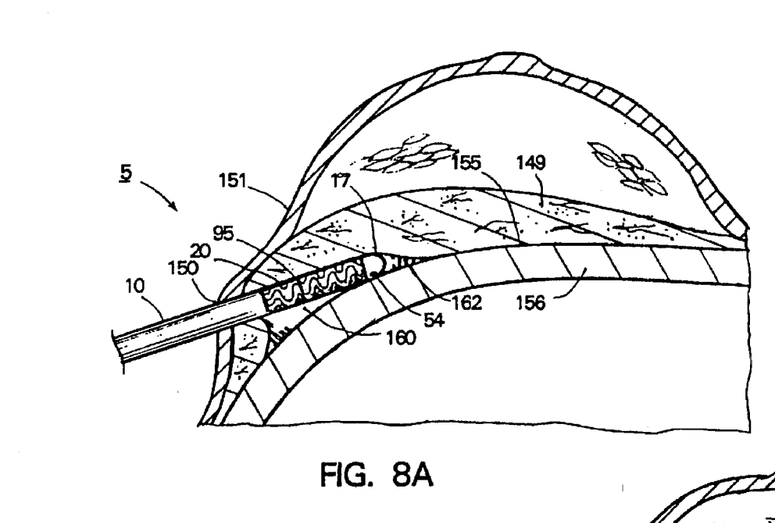
FIGS. 8A–8C are sectional views of a patient's chest taken along lines 8A—8A, 8B—8B and 8C—8C of FIGS. 7A, 7B and 7C.
Figure 8B:
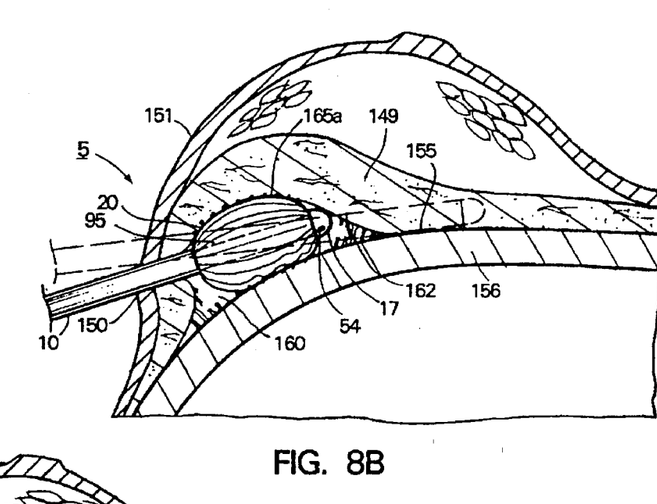
Figure 8C:
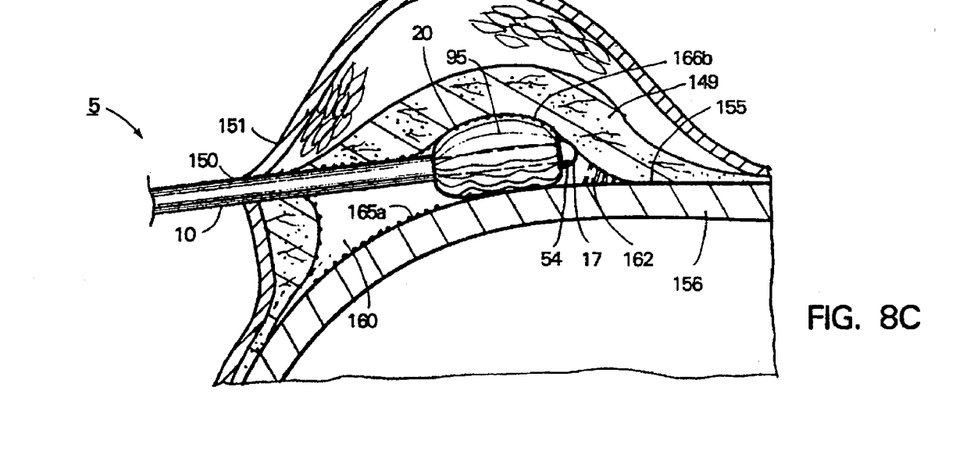

The use of EC dissector 5 of FIG. 1 in performing a method in accordance with the present invention now may be described briefly in dissecting and cauterizing the plane between the pectoralis major muscle and the anterior chest wall to receive a prosthesis as shown in cartoons (FIGS. 7A-7C) and corresponding sectional views (FIGS. 8A-8C).

The various external connections are made to the instrument including video camera 39 fitted to eyepiece 37. A conventional LG (light source) is connected to fitting 48. An inflation/deflation source is connected to Luer-type fitting 53 and an EC source is connected to fitting 103.

Referring to FIG. 7A, assume that the surgical objective is dissection of a plane under pectoralis major muscle 149 on the patient's right side to place a prosthesis under the patient's right breast. The patient is prepared with a suitable anesthesia and the surgeon makes a small incision 150 in skin layer 151 lateral to the breast as shown in FIGS. 7A (see also FIG. 8A). The surgeon inserts the distal tip 17 of probe 10 into incision 150 and then pushes tip 17 inward into plane 155 overlying the anterior chest wall 156 and underlying pectoralis major muscle 149 (see FIG. 8A).

The surgeon then pushes blunt tip 17 inward (distally) along plane 155 thus creating dissected pathway 160 (see hatched area of FIG. 7A). While advancing probe sleeve 10, the surgeon views the progress of tip 17 on a video monitor (not shown). As the surgeon applies axial pressure on probe 10, the blunt distalmost tip 17 tends to follow the line of least resistance, i.e., along plane 155 overlying chest wall 156 and beneath muscle 149 (see FIG. 8A).

As an option, the surgeon may direct an assistant to supply an insufflation medium, such as $CO_2$, under pressure through insufflation tube 50 to insufflate the dissected plane 160 just in front of tip 17 (see FIG. 8A). Such contemporaneous insufflation with $CO_2$ together with a back and forth movement of tip 17 provides improved vision of dissected plane 160 and allows viewing of anatomic structures.

A shown in FIGS. 7B and 8B, the surgeon stops advancing tip 17 and inflates sleeve 20 by pressing trigger arm 66a to further dissect plane 155. A fluid medium expands sleeve 20 to the previously described expanded dimensions at a preferred pressure ranging from 0.01 psi to 5.0 psi. The elastic characteristics of wall 19 of sleeve 20 causes dissection of connective tissues 162 along lines of least resistance within plane 155. Such dissection generally causes minimal damage to blood vessels but due to the profuse blood supply in plane 155, some blood vessels will be disrupted and severed. With sleeve 20 in the expanded state of FIG. 8B, the surgeon depressed EC trigger 115 to deliver electrical current intermittently to electrodes within grid 95 causing the electro-cauterization of "zone" 165a around the expanded sleeve. The surgeon then deflates sleeve 20 by depressing trigger arm 66b and again advances tip 17 inward as shown in FIG. 8B in phantom view to dissect an additional track 160. By repeating the above-described procedures, the surgeon dissects and cauterizes the "zone" 165b. Thereafter, the entire plane underlying the pectoralis major muscle 149 may be dissected and cauterized using similar methods.

The implantation of the breast prosthesis may be completed by inserting the prosthesis through incision 150. The incision may have to be increased in length to about 2 cm. or more to introduce the prosthesis therethrough.

3. Dual-Port Cannula and Skin Seal

At times, it may be useful to further cauterize the margins around dissected plane 160 after dissection with EC dissector 5. For that reason, another instrument in accordance with the present invention for facilitating a breast implant procedure is a dual-port cannula assembly 200 shown in FIGS. 9–12.

Figures 17A, 17B:
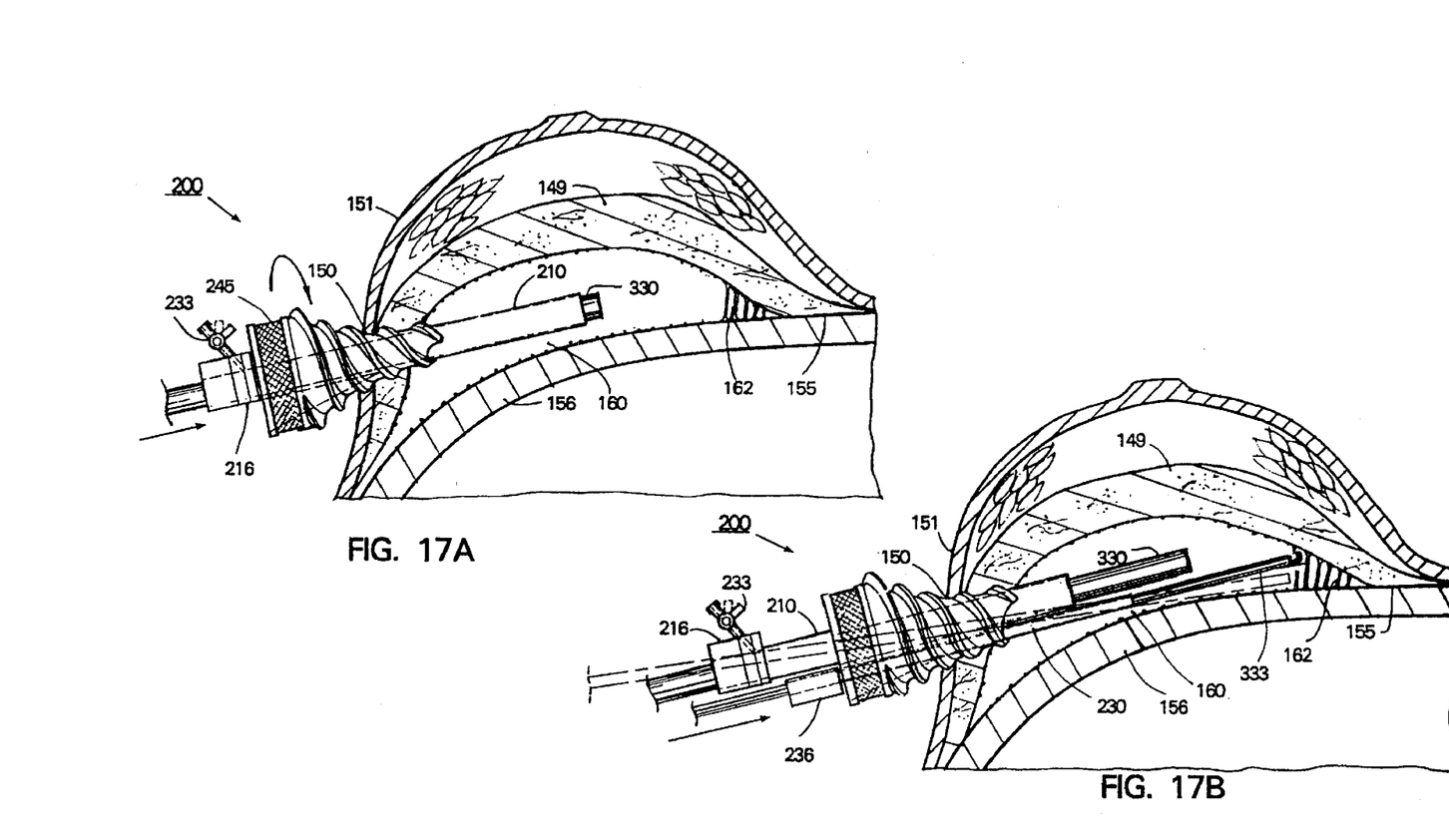

Dual-port cannula assembly 200 differs from commercially available devices in that a single device adapted for use in a single incision includes a 10–12 mm. diameter port (not limiting) to accommodate an endoscope and a 5 mm. diameter port (not limiting) to accommodate a 3 mm. to 5 mm. diameter accessory instrument (e.g., an electro-cautery hook) as shown in FIG. 17A. Dual-port cannula assembly 200 also provides an improved fluid-tight skin seal that is adapted for providing a seal in soft tissue and various size incisions while at the same time providing a somewhat flexible connection between the dual ports of cannula assembly 200.

Figure 9:
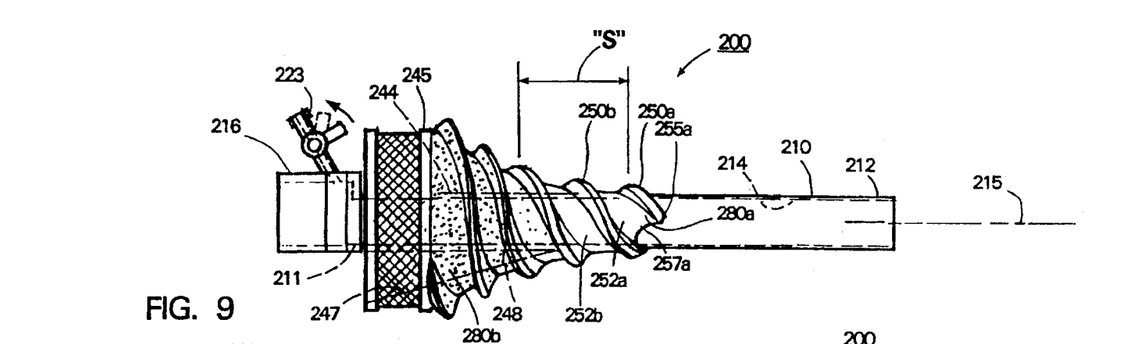
FIG. 9 is a side elevational view of the cannula assembly of the present invention.

More particularly referring to FIG. 9, dual-port assembly 200 has a 10–12 mm. diameter first tubular port 210 with proximal and distal ends, 211 and 212. First tubular port 210 is made of any suitable material such as metal, plastic or glass-fiber with central bore or passageway 214 extending along axis 215. Proximal end 211 of the cannula is fixed in first port housing 216. Housing 216 is made of plastic mating halves that seal and enclose hollow interior 218. An improved instrument seal 222 further described below is secured in the proximal portion of first housing 216 to seal interior 218 and is flexible to also provide a fluid-tight seal around the shaft of an endoscope pushed through the seal. Luer-type fitting 223 communicates with interior 218 of first housing 216 and bore 214 of tubular port 210 to introduce an insufflation medium therethrough.

Figures 10, 11, 12:
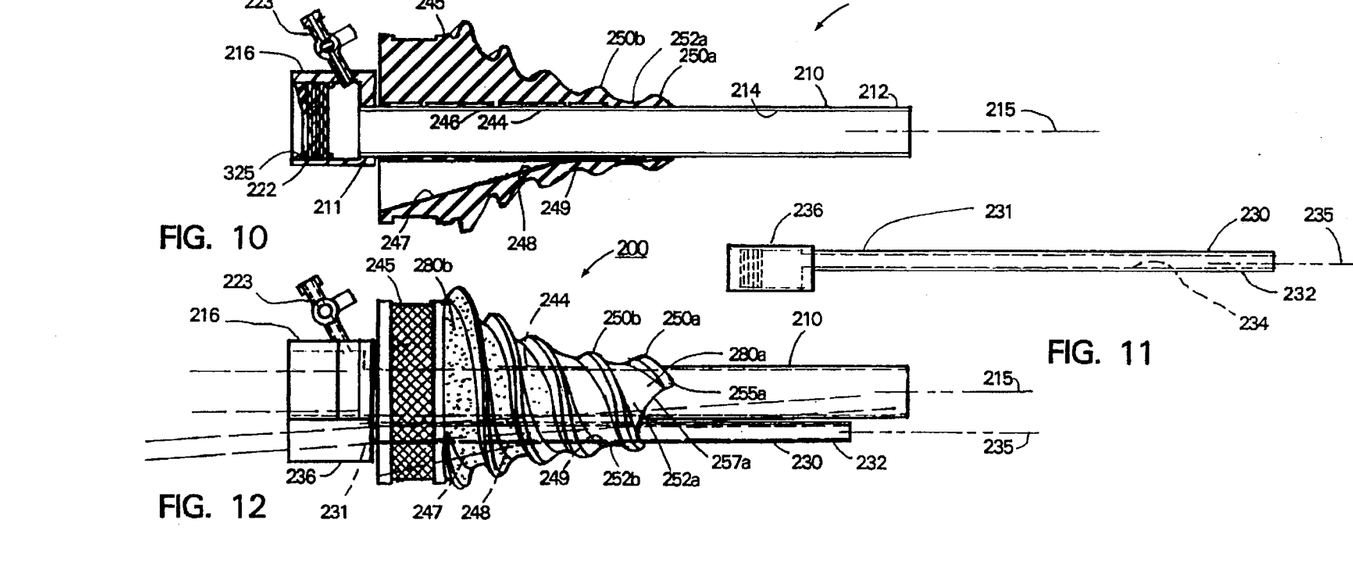
FIG. 10 is a longitudinal sectional view of the cannula assembly of FIG. 9 taken along line 10—10 of FIG. 9 rotated 90°.
FIG. 11 is a side elevational view of a removable port for use with the cannula assembly of FIG. 9.
FIG. 12 is a side elevational view of the assembly of the cannula of FIG. 7 and the removable port of FIG. 9.

Referring to FIG. 11, removable second tubular port 230 with proximal and distal ends, 231 and 232 has bore 234 with a diameter of approximately 5 mm. (not limiting). Second tubular port 230 is made of any suitable material such glass-fiber and its centerline extends along axis 235. Proximal end 231 of the second tubular port 230 is fixed in second port housing 236 along with an instrument seal further described below.

Referring to FIGS. 9–10, first tubular port 210 is slidably mounted in bore 244 in skin seal member 245. Skin seal 245 is made of a resilient material such as urethane with molded helical threads having an increasing transverse sectional dimension in the proximal direction for screwing into an incision ranging in length from 1 cm. to 3 cm. First tubular port 210 is slidably and slidably positioned at any depth in bore 244 by resilient partly-annular gripping webs 246 molded around central bore 244 (see FIGS. 10, 13 and 14).

Second tubular port 230 may be introduced through flared portion 247 of longitudinal passageway 248 that extends through skin seal 245 that is radially outward from bore 244. The distal portion of passageway 247 has a collapsible portion 249 that is collapsed in a repose state and may be expanded in a tensioned state as shown in FIG. 12 when second tubular port 230 is pushed therethrough. Thus, referring to FIG. 12, it can be seen that second tubular port 230 may be slid entirely through passageway 247 in skin seal 245 to provide a second port capable of accommodating a 3 mm. to 5 mm. accessory instrument. Both ports, 210 and 230, may be adjusted for depth (and sealed) in skin seal 245 to suit a surgical procedure by sliding the ports through passageways 244 and 248 respectively.

Referring to FIG. 12, it should be noted that second tubular port 230 may be flexed relative to first tubular port 210 because the resilient material of skin seal 245 provides a flexible connection. FIG. 12 shows in phantom views a limited range of motion provided to instrument shafts within the first and second ports.

Referring to FIGS. 9 and 12, skin seal 245 has dual-lead helical threads 250a and 250b although single-lead and plural-lead threads fall within the scope of the present invention. Helical channel portions 252a and 252b lie between threads 250a and 250b. The distalmost termination of each thread, for example projecting thread margin 255a of thread 250a, projects distally beyond receding margin 257a of channel 252a that defines the termination of bore 244 in the skin seal. Such receding margin portion 252a of a channel insure that the distalmost thread margins 255a (255b not visible) helically engage tissue instantly upon axial/helical movement of seal 245 into an incision. Such immediate helical engagement is to be contrasted with commercially-available threaded seals typically having threads that engage tissue only after a tubular portion of the seal is pushed axially into an incision.

Figures 13, 14:
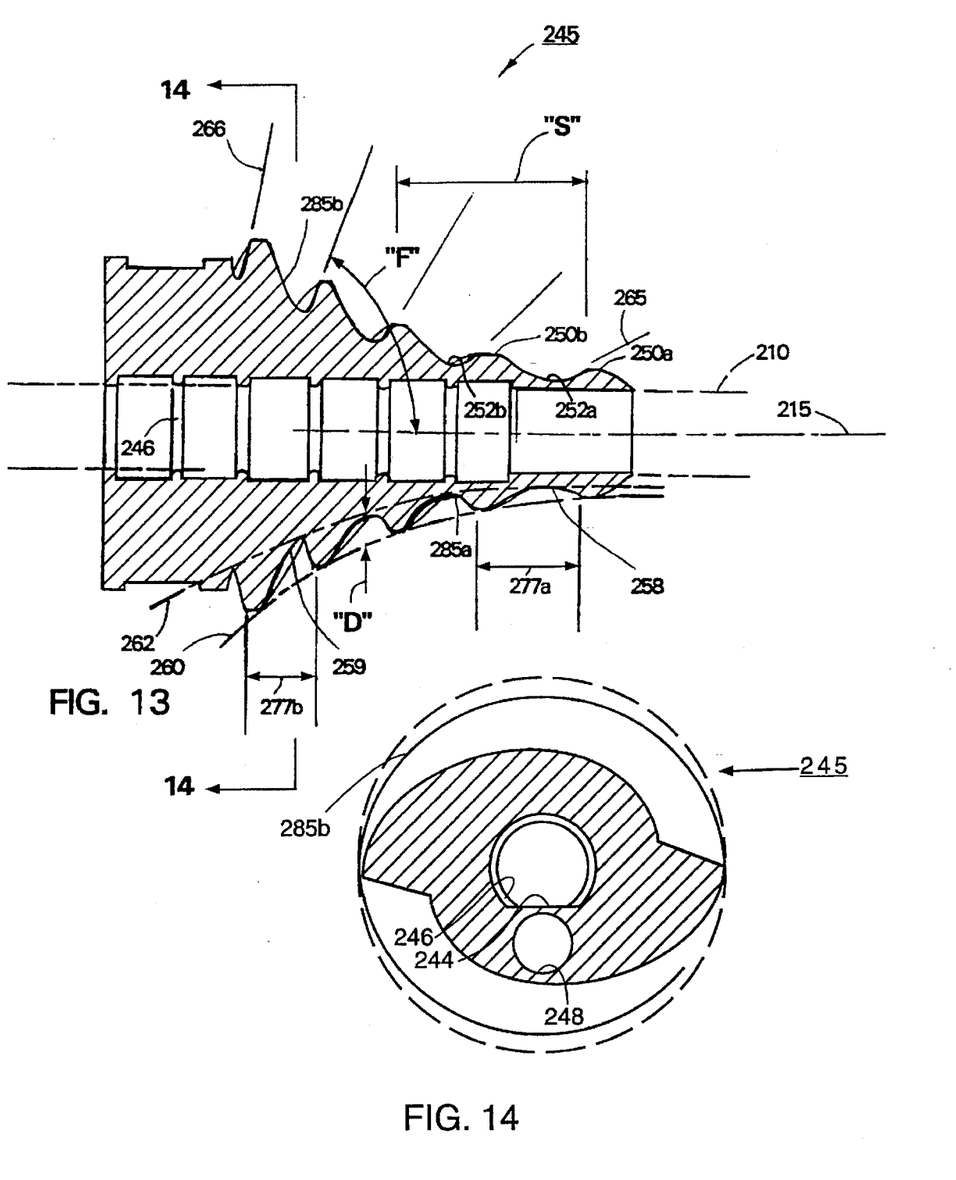
FIG. 13 is an enlarged longitudinal sectional view of the skin seal similar to FIG. 10.
FIG. 14 is a transverse sectional view of the skin seal of FIG. 13 taken along line 14—14 of FIG. 13.

Of particular interest to skin seal 245, referring to FIG. 13, its "fluid-tight" sealing capabilities within a skin incision are enhanced by providing helical threads 250a and 250b with variable thread depth "D" in which the threads increase in depth in the proximal direction from distal shallow thread portions 258 (collectively) to proximal deep thread portions 259 (collectively). The thread depth may range from 0.001" to 0.010" in distal portion 258 and range from 0.010" to 0.300" in proximal portion 259. Thread depth "D" is herein defined as the radial dimension between thread periphery 260 and channel periphery 262.

Of particular interest to skin seal 245, referring to FIG. 13, its "fluid-tight" sealing capabilities within skin incisions up to 2 to 3 cm. in length are variable-angle thread faces "F" in which proximal thread faces increase in angle relative to axis 215 in the proximal direction from lesser-angled face portions 265 (collectively) to greater-angled face portions 266 (collectively). The face angles may range from 15° to 30° in distal portion 265 and range from 45° to 90° in the proximal portion 266. The thread portions with deeper threads and more steeply-angled faces more securely engage tissue and prevent tissue from slipping over the thread.

Of particular interest to skin seal 245, its "fluid-tight" sealing capabilities within an incision are enhanced by providing helical threads 250a and 250b that increase in transverse sectional dimension at an increasing rate. That is, thread periphery 260 when viewed in longitudinal section has a part-parabolic type shape. Thread periphery 260 in a 10 mm. tubular port preferably increases parabolically in a transverse section from approximately 0.450" to 0.550" at the distal end to approximately 1.0" to 1.6" over a length of 1.25" to 2.00". Such parabolic thread periphery 260 is preferred because only a small angular rotation of such a skin seal 245 is required to improve the device's sealing effect within various length incisions or in an incision which stretches or tears. Such parabolic thread periphery 260 is to be contrasted with cone-shaped threads of existing skin seals. Referring to FIG. 13, a parabolic-thread skin seal 245 will seat tightly in less-stretchable skin layer while at the same time causing relatively less stretching or tearing of soft interior tissues, such as subcutaneous tissue and muscles.

Of particular interest to skin seal 245, referring to FIG. 13, its "fluid-tight" sealing capabilities in an incision are enhanced by providing helical threads 250a and 250b with a variable spiral-lead "S" by which is meant threads 250a and 250b decrease in spiral-lead dimension in the proximal direction from a distal fast-lead portion 277a to a proximal slow-lead portion 277b. Spiral lead "S" is defined as the axial travel resulting from an angular movement of 360° of a radial line extending radial outward from axis 215 as the line passes through threads 250a and 250b. Such variable-lead threads are an improvement over existing constant spiral-lead threads in skin seals in that the reducing spiral lead progressively engages and compacts tissue tightly into channels 252a and 252b between threads 250a and 250b thereby making the sealing effect between tissue and the surface of skin seal 245 more fluid-tight.

Of particular interest to skin seal 245, the seal has "resistance-to-rotation" capabilities to maintain itself in an incision in skin by providing helical threads 250a and 250b, and channels 252a and 252b with a surface finish that is variably-textured for frictionally engaging tissue. Referring to FIGS. 9 and 12, distal smooth-surface portion 280a of seal 245 has a mirror finish with the seal's surface progressively more textured in the proximal direction transitioning to proximal rough-surface portion 280b, having a sandblast-type finish. Thus, as seal 245 is helically advanced into an incision in skin, the increasingly rough surface finish will cause increased frictional engagement with skin and tissue to prevent seal 245 from rotating in the incision. The distal smooth-surface portion 280a allows for ease of rotation as seal 245 starts helical engagement in an incision. The skin seal alternatively may incorporate variably "sticky" types of rubber compounds to achieve the desired effect.

Of particular interest to skin seal 245, its "resistance-to-rotation" capabilities in an incision are enhanced by providing either helical threads, 250a and 250b, or helical channels 252a and 252b with a non-round, for example a slightly oval, transverse sectional shape to prevent its easy rotation in tissue. Referring to FIGS. 13–14, the medial and proximal portion, 285a and 285b respectively, of skin seal 245 have an oval sectional shape. Thus, as skin seal 245 is helically advanced into incision 150 in skin layer 151 (see FIG. 17A), the radial inward pressure caused by tissue will resist rotation. The degree of ovality as shown in FIG. 14 (cf. round-shape in phantom view) also may increase in the proximal direction for increased engagement with tissue as the sectional dimension of skin seal 245 increases thus preventing rotation in the incision.

Of particular interest to skin seal 245, its "fluid-tight" seal capabilities in an incision, including its capability to helically engage tissue, are maintained even as the transverse sectional shape of the resilient seal is deformed to some extent by the introduction (or withdrawal) therethrough of second tubular port 230. That is, the skin seal's function of screwing into incision 150 is provided no matter whether dual-port cannula assembly 200 is utilized in a single-port or dual-port configuration. It should be appreciated that such a flexible skin seal 245 may be used in any cannula assembly without a second port.

Figures 15, 16:
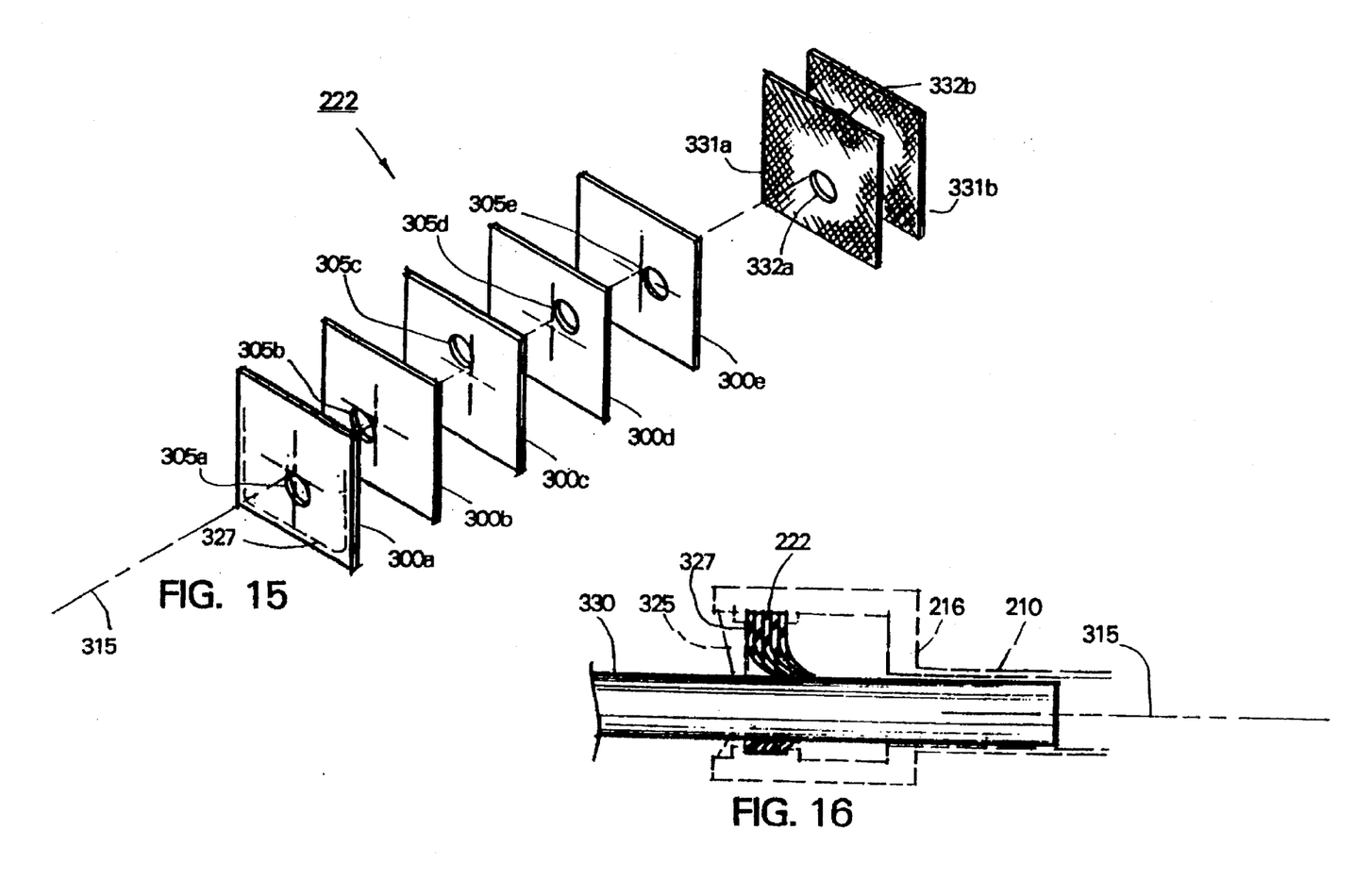
FIG. 15 is isometric view of a seal of the cannula assembly of FIG. 9.
FIG. 16 is sectional view of the seal of FIG. 15 with an instrument pushed through the seal.

As shown in FIGS. 15–16, a simplified type of fluid-tight instrument seal 222 is adapted for first and second tubular ports 210 and 230 and is mounted, for example in housing 216. "Multi-shutter" instrument seal 222 comprises a sandwich of 5 (not limiting) separate elastomeric "shutters", 300a–300e, each made from a sheet material such as latex having a thickness ranging from 0.001" to 0.50". The number of shutter elements may vary from 4 to 20 depending on the thickness of each shutter. Each shutter element 300a–300e includes a respective aperture 305a–305e, that is approximately 1 mm. to 3 mm. (not limiting) in diameter. Each aperture 305a–305e, has a circumferential edge that intersects or comes close to intersecting axis 315 of a tubular port. The centerline of each such aperture 305a–305e, is disposed at a sequential radial angle around axis 315. For example, FIG. 15A depicts five flexible shutters 300a–300e, and the center of each aperture being 72° apart radially with respect to axis 315. Thus, it can be seen that by sandwiching shutters 300a–300e tightly together in FIG. 16, the apertures 305a–305e are misaligned providing a seal to prevent the flow of fluids axially therethrough. FIG. 16 shows distensible guide aperture member 325 to direct the distal tip of instrument into the center of seal 222. Flexible shutters 300a–300e are secured together at seal perimeter 327 by adhesives or any other suitable means for fixing by adhesives in a tubular port housing.

As depicted in FIG. 16, the introduction of endoscope 330 in the distal direction through seal 222 along axis 315 causes each shutter to stretch until each respective aperture 305a–305e is aligned along axis 315 to accommodate the passage of the instrument. With endoscope 330 extending through seal, each shutter 300a–300e flexibly seals around the shaft of the instrument.

It should be appreciated that one or more additional "wiper" shutters 331a–331b (see FIG. 15) may be included distally from shutters 300a–300e and be made of an absorbent elastomeric material such as a cotton/Lyrca® blend for the purpose of absorbing and cleaning fluids, secretions and tissue from the surfaces of instruments passing through seal 222 in either direction. Such "wiper" shutters have misaligned apertures 332a–332b as described above and help prevent contamination of seal 222 and are particularly useful for cleaning the lens of an endoscope passing distally through seal 222.

4. Method of Use of Dual-Port Cannula

Operation of dual-port cannula assembly 200 in performing a method in accordance with the present invention is described with reference to FIGS. 17A–17B. After dissected plane 160 is created with EC dissector 5, dual-port cannula assembly 200 is screwed into incision 150. The dissected plane 160 may be insufflated through Luer-type fitting 223 to provide a working space as shown in FIG. 17A. Endoscope 330 is introduced through first tubular port 210. Such a conventional endoscope 330 may be preferred over EC dissector 5 for endoscopic viewing because EC dissector 5 has optics generally suited for blunt dissection. As shown in FIG. 17B, the depth of tubular port 210 within skin seal 245 may be adjusted by sliding the port inward or outward.

Referring to FIG. 17B, second tubular port 230 is inserted through skin seal 245 of the cannula assembly 200. Thereafter, an accessory instrument (e.g., an EC probe 333) is introduced through second port 230 to prepare dissected plane 160 for introduction of a prosthesis. The EC probe 333, for example, is utilized to push or dissect tissues around the margin of dissected space 160 and to cauterize vessels as shown in FIG. 17S. As can be seen in FIG. 17S in phantom view, the dual ports, 210 and 230 are resiliently connected allowing a range of movement between endoscope 330 and EC stick 333 as cannula assembly 200 is rotated in incision 150. Thus, endoscope 330 may be held stable to stabilize the image on a video monitor (not shown) as EC prove 333 is manipulated.

5. Electro-Cauterizing "Inside-Out" Trocar

Figures 18, 19A, 19B:
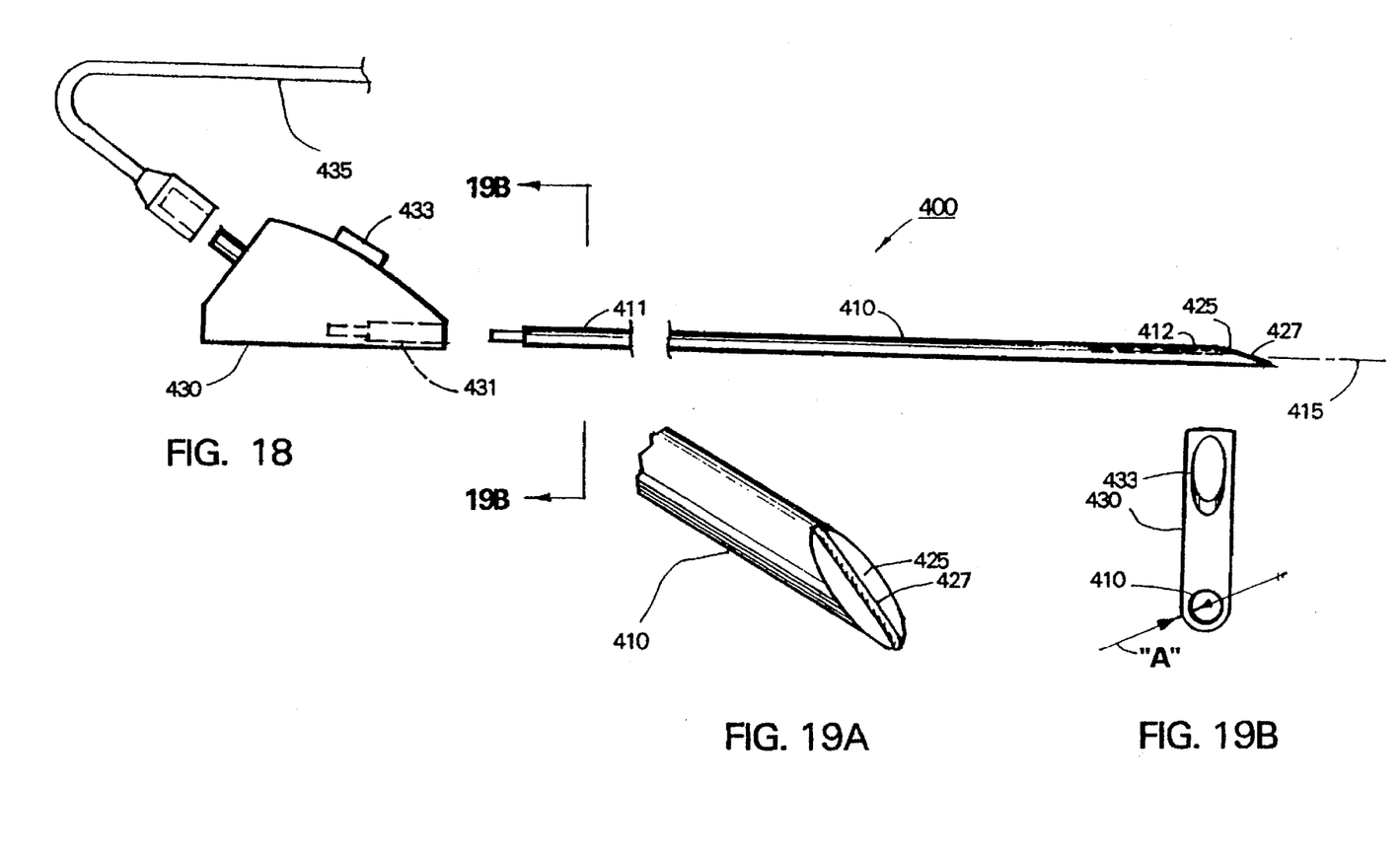
FIG. 18 is a side elevational view of a trocar of the present invention.
FIGS. 19A–19B are other views of the trocar of FIG. 18.

At times, it may be necessary to introduce another accessory instrument into dissected (and insufflated) plane 160 which may require yet another cannula in an additional incision. For that reason, another instrument in accordance with the present invention for facilitating a breast implant procedure is "inside-out" electro-cauterizing (EC) trocar 400 (see FIGS. 18–19B).

In co-pending and commonly invented application Ser. No. 08/255,273, now U.S. Pat. No. 5,569,183, an elongate trocar was disclosed for making an additional incision from inside the body to outside the body. Such an "inside-out" trocar was introduced through a working channel in a dissector that was disposed inside a dissected plane. The sharp trocar tip was adapted to be pushed outward from the dissected plane under endoscopic vision through the skin to provide an incision for an additional cannula. The method of providing a additional incision from the inside to the outside is far safer than plunging a sharp trocar tip inward, especially when dealing with a restricted-size insufflated space.

Referring to FIG. 18, a device in accordance with the present invention includes an electro-cauterizing (EC) trocar 400 with elongate cylindrical shaft 410 made of plastic or other suitable material and having proximal and distal ends, 411 and 412. The diameter of shaft 410 is preferably 3 mm. to 5 mm. (not limiting) along axis 415. The distal end of shaft 410 preferably has a distal slanted face 425 with a mono-polar electrode 427 extending diametrically across the elongate axis of face 425. It should be appreciated that a face angle may range from e.g. 20° to 90° relative to axis 415. The electrode 427 is adapted to extend diametrically across the longer axis of a distal face so that the advancement of face 425 through tissue results in a single linear electro-cauterized slit in tissue (see FIG. 19A).

The shaft 410 of EC trocar 400 is disposable and is removably mountable within handle 430. A conventional electrical source of the type employed for surgical electro-cauterizing instruments is connected to handle 430 and includes an internal electrical socket 431 with push-on type fitting to couple handle 430 with the proximal end of shaft 410. Trigger 433 is provided to send electrical current to electrode 427. Cable 435 is connected to an electrical source. FIG. 19B is an end elevational view of handle 430 illustrating its three flat sides that extend radially outward a minimal dimension "A" beyond the diameter of shaft 410 for reasons explained below. The maximum dimension "A" preferably is 2 to 3 mm. or less and is comparable to the similar EC dissector of FIGS. 1–3.

It should be appreciated that an "inside-out" EC trocar (not shown) may be provided with shaft having a diameter of about 10 mm. including an interior lumen for accommodating an endoscope. Such an "inside-out" trocar would be similar to the instrument disclosed in application Ser. No. 08/255,273, now U.S. Pat. No. 5,569,183, with the addition of an EC electrode.

6. Method of Use of Electro-Cauterizing "Inside-Out" Trocar

Operation of EC trocar 400 in conjunction with dual-port cannula assembly 200 in performing a method in accordance with the present invention may be described with reference to FIGS. 20A–20B. Assume that EC dissector 5 has been utilized along with cannula assembly 200 to dissect and insufflate plane 160 as shown in FIG. 20A.

Assume the surgeon that uses EC dissector 5 as an endoscope introduced through first tubular port 210. The surgeon then introduces EC trocar 400 through second tubular port 230 and directs trocar tip under endoscopic vision to a safe location for an "inside-out" incision. Thereafter, the surgeon pushes the EC trocar's tip 417 outward under slight pressure and depresses trigger 433 to deliver electrical current to electrode 427 causing incision 444 to be made with slight forces on the instrument. The surgeon may view the patient's skin tent outwardly as the distal tip projects outwardly from the incision at which time he releases trigger 433 to stop the flow of current. Thereafter, as shown in FIG. 20B, the surgeon inserts a cannula assembly 500 into incision 444 over shaft 410 of EC trocar 400 using the trocar shaft as a guide. The cannula typically may be a 5 mm. cannula but is shown in FIG. 20B with a 10 mm. cannula with a tapered expander member 510 disposed in the bore of the cannula. The EC trocar 400 then is withdrawn. The surgeon thus is provided with two cannula assemblies in two incisions to complete the breast implant procedure.

The use of EC trocar 400 is an improvement over conventional sharp-edged trocars in that very little pressure is required to create an incision through tissue. The leading edge of trocar tip does not need to be sharp as the electrode will incise tissue. Further, the EC trocar will cauterize dissected blood vessels to limit blood within the dissected space 160.

Figures 20A, 20B:
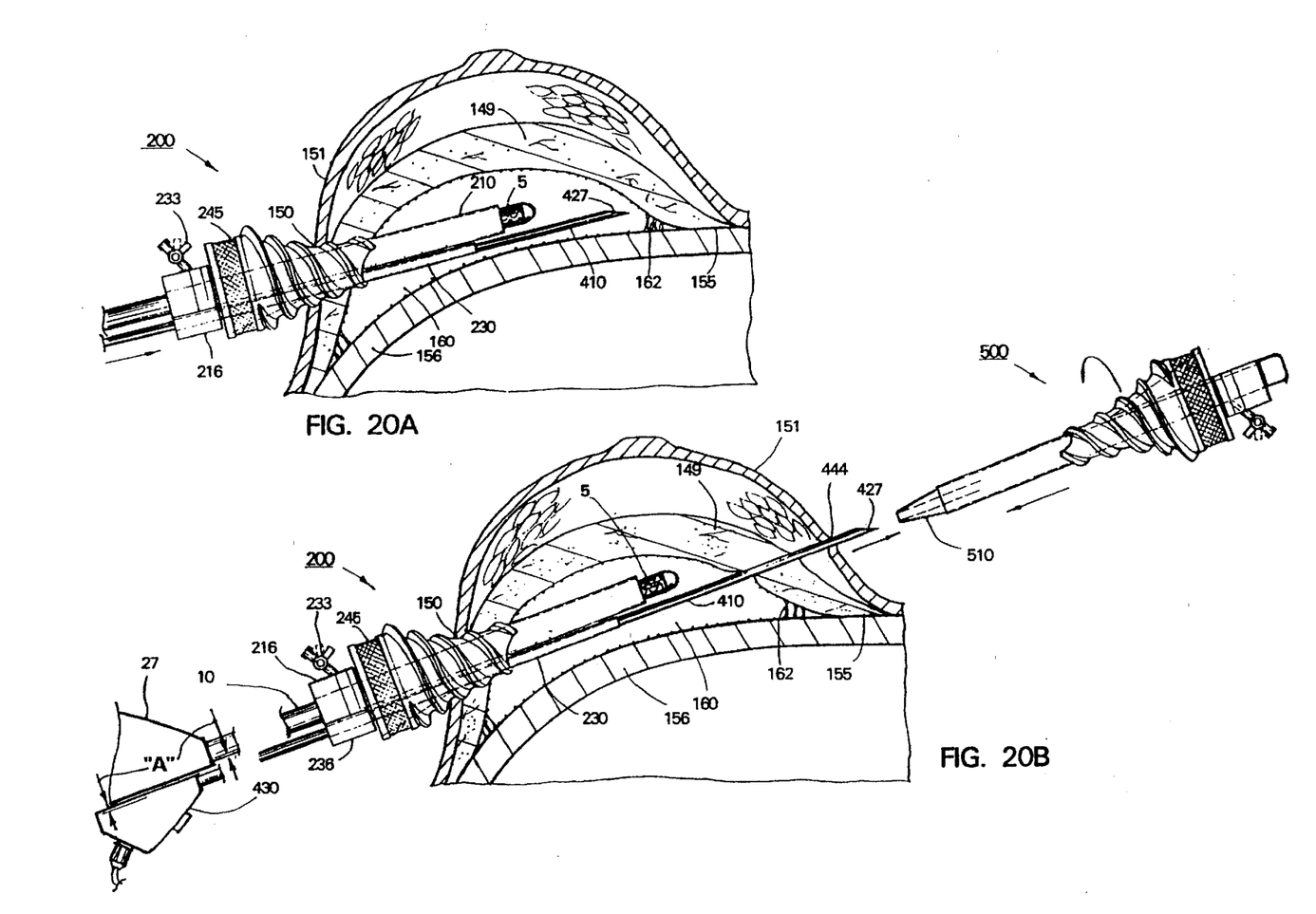
FIGS. 20A–20B are sectional views of a patient's chest showing the manner in which the trocar of FIG. 18 is utilized to perform an exemplary method of the present invention.

As shown in FIG. 20B, the handle 27 of EC dissector 5 may be angularly oriented so that its flat sides of probe sleeve 10 do not interfere with the similarly configured sides of handle 430 of EC trocar 400. Thus, instrument handles that extend radially outward a minimal dimension "A" beyond the diameter of the instrument shaft may be manipulated when side by side in dual-port cannula assembly 200.

The above-described EC dissector 5 includes built-in endoscopic viewing lenses and fiber optic LG (light guide). It should be appreciated that an instrument with an inflatable EC structure may be adapted with a longitudinally-extending lumen to receive a conventional endoscope. Although the present disclosure is directed to dissecting and cauterizing a plane between the chest wall and overlying pectoralis major muscle, it should be appreciated that the device and method can be used for other surgical procedures. For example, the instrument and method can be used for any procedure in which it is useful to dissect and cauterize planes around muscles.

This disclosure is illustrative and not limiting. Further variations will be apparent to one skilled in the art in light of this disclosure and are intended to fall within the scope of the appended claims.

What is claimed is:

1. An instrument for dissecting and cauterizing in an interior of a body comprising:

an elongate probe member extending along a longitudinal axis;

an inflatable structure having an inflation chamber and carried around a distal portion of said probe member and in a contracted state having a diameter about equal to the diameter of said probe member and in an expanded state having a greater transverse dimension than that of said contracted state;

an inflation mechanism operatively connected to said inflation chamber thereby to inflate and deflate said inflatable structure between said contracted state and said expanded state; and an electro-cautery grid comprising a plurality of electrodes carried around an exterior of said inflatable structure, said electrodes operatively connected to an electrical source, said electro-cautery grid being adapted for cauterizing dissected blood vessels;

wherein in said contracted state said electrodes are in an at least partly radial pattern, so that in said expanded state, said at least partly radial pattern is expanded by said inflatable structure to a straightened longitudinal pattern.

2. The instrument of claim 1, wherein said electro-cautery grid is actuatable with said inflatable structure in any state intermediate said contracted and expanded states.

3. The instrument of claim 1, further including:

an optical viewing structure extending through said probe member for viewing from said proximal end of said probe member through a distal tip of said probe member; and a light-transmitting structure extending through said probe member for transmitting light from said proximal end through said tip.

4. The instrument of claim 3, wherein said tip is blunt and transparent.

5. The instrument of claim 3, wherein said optical viewing structure and said light-transmitting structure together comprise an endoscope disposed in a longitudinally-extending lumen in said probe member.

6. The instrument of claim 1, wherein said inflatable structure is at least partly an elastomeric material.

7. The instrument of claim 1, wherein said probe member defines a longitudinally-extending channel extending from said proximal end through said distal tip of said probe member for delivering an insufflation medium.

8. The instrument of claim 1, wherein said electrodes are bi-polar.

9. The instrument of claim 1, wherein said electro-cautery grid is connected to an electrical source adapted to send an electrical current in sequence to a first electrode for a predetermined time, then to a second electrode adjacent to said first electrode for a predetermined time, then to at least a third electrode for a predetermined time, thereby causing a locally intermittent electro-cauterizing effect that sequentially moves around the surface of said inflatable structure.

10. A method for dissecting connective tissues, comprising the steps of:

introducing a distal blunt tip of an elongate probe into a plane in the interior of the body in a first location;

advancing said blunt tip distally along said plane to a second remote location thereby creating a small diameter dissected track;

expanding an inflatable structure at said blunt tip thereby further bluntly dissecting connective tissues along said plane in said second location; and passing an electrical current into an electrode grid on a surface of said inflatable structure, thereby cauterizing dissected blood vessels around said inflatable structure in said second location.

11. The method of claim 10, wherein said electrode grid has a plurality of electrodes, and the passing step includes passing an electrical current sequentially into each electrode of said grid around said surface of said inflatable structure.

12. The method of claim 10, wherein the introducing step is preceded by a step of making an incision though overlying tissue to access said plane.

13. The method claim 10, wherein the advancing step includes the step of viewing through said probe the plane being dissected around said tip.

14. The method claim 10, wherein the advancing step includes the step of insufflating the dissected plane with a fluid flowing through said tip.

15. The method of claim 10, wherein the advancing step includes the step of actuating said electro-cautery grid around said inflatable structure in its contracted state thereby cauterizing dissected blood vessels along said track.

16. The method claim 10, further comprising the steps of:

deflating said inflatable structure to its contracted state;

advancing said blunt tip distally along said plane to at least one additional location, thereby creating a small diameter dissected track;

expanding said inflatable structure at said blunt tip, thereby further bluntly dissecting connective tissues along said plane in said at least one additional location; and passing an electrical current into said electrode grid, thereby cauterizing dissected blood vessels around said inflatable structure in said at least one additional location.

* * * * *